United States Patent [19]
Wilk

[11] Patent Number: 5,535,759
[45] Date of Patent: Jul. 16, 1996

[54] ENDOSCOPIC METHOD OF CLEANING AND OPERATING ON A SITE WITHIN A PATIENT

[76] Inventor: Peter J. Wilk, 185 W. End Ave., New York, N.Y. 10023

[21] Appl. No.: 344,380

[22] Filed: Nov. 23, 1994

Related U.S. Application Data

[63] Continuation-in-part of Ser. No. 333,363, Nov. 2, 1994.

[51] Int. Cl.⁶ .................................................. A61B 19/00
[52] U.S. Cl. ........................ 128/898; 606/113; 606/205; 600/156
[58] Field of Search ............................... 604/19, 21, 22, 604/24, 43, 49, 53, 93, 264, 282; 600/153, 156; 606/1, 110, 113, 43–50, 205–209; 128/898

[56] References Cited

U.S. PATENT DOCUMENTS

| | | | |
|---|---|---|---|
| 404,946 | 6/1889 | Andersson | 43/11 |
| 460,940 | 10/1891 | Baugh | 606/106 |
| 1,585,483 | 5/1926 | Freer | 43/7 |
| 1,609,014 | 11/1926 | Dowd | 606/114 |
| 1,652,327 | 12/1927 | Richter | 604/21 |
| 3,472,230 | 10/1969 | Fogarty | 606/127 |
| 3,527,203 | 9/1970 | Gravlee | 128/750 |
| 3,715,829 | 2/1973 | Hamilton | 43/12 |
| 3,735,751 | 5/1973 | Katz | 604/24 |
| 4,040,413 | 8/1977 | Ohshiro | 604/21 |
| 4,073,287 | 2/1978 | Bradley et al. | 604/21 |
| 4,202,338 | 5/1980 | Bitrolf | 606/47 |
| 4,326,530 | 4/1982 | Fleury, Jr. | 606/47 |
| 4,345,599 | 8/1982 | McCarrell | 606/113 |
| 4,493,320 | 1/1985 | Treat | 606/47 |
| 4,503,855 | 3/1985 | Maslanka | 606/47 |
| 4,516,347 | 5/1985 | Dickie | 43/11 |

(List continued on next page.)

FOREIGN PATENT DOCUMENTS

| | | | |
|---|---|---|---|
| 0025796 | 1/1884 | Brazil | 606/127 |
| 0046856 | 5/1889 | Germany | 606/45 |
| 2938259 | 4/1981 | Germany | 606/47 |
| 3347122 | 6/1985 | Germany | 606/47 |

OTHER PUBLICATIONS

Waye, J. D. et al. "The Lost Polyp: A Guide To Retrieval During Colonoscopy" Int. J. Colorect. Dis. (1988) 3:229–231.

Ricca, J. J. "Retrieval of Polyps Severed at Colonoscopy" Gastrointestinal Endoscopy (1977) 24, 1:44.

Maas, L. C. et al. "Polyp Retrieval Impossible without Colonoscope Tip" and Ward, W. J. Reply Gastrointestinal Endoscopy (1984) 30, 6:378.

(List continued on next page.)

*Primary Examiner*—Stephen C. Pellegrino
*Assistant Examiner*—Glenn Dawson
*Attorney, Agent, or Firm*—R. Neil Sudol; Henry D. Coleman

[57] ABSTRACT

A surgical method utilizes an endoscope with an elongate flexible insertion member and (i) an endoscopic instrument guide having a plurality of lumens, (ii) a flexible irrigation member slidably insertable through one of the lumens and (iii) an auxiliary endoscopic surgical instrument slidably insertable through another of the lumens. The irrigation member has a distal end provided with a multiplicity of apertures spaced from one another both longitudinally and circumferentially. Upon introduction of the endoscope insertion member into a patient, the endoscopic instrument guide is moved through the biopsy channel so that a distal end of the endoscopic instrument guide emerges from the biopsy channel. The irrigating member is then slid through endoscopic instrument guide so that the distal end of the irrigation member emerges therefrom. Upon operatively connecting a proximal end of the irrigation member to a source of pressurized liquid, liquid from the source is sprayed in a substantially uniform cylindrical distribution through the apertures at the distal end of the irrigation member, thereby cleaning organic debris from a site inside the patient. A distal end portion of the auxiliary endoscopic surgical instrument is ejected from the endoscopic instrument guide and used to perform an operation on organic tissues at the cleaned site inside the patient.

8 Claims, 4 Drawing Sheets

U.S. PATENT DOCUMENTS

| | | | |
|---|---|---|---|
| 4,551,129 | 11/1985 | Coleman et al. | 604/21 |
| 4,557,255 | 12/1985 | Goodman | 606/127 |
| 4,638,802 | 1/1987 | Okada | 606/47 |
| 4,643,187 | 2/1987 | Okada | 606/47 |
| 4,661,094 | 4/1987 | Simpson | 604/53 |
| 4,681,122 | 7/1987 | Winters et al. | 128/784 |
| 4,705,041 | 11/1987 | Kim | 606/108 |
| 4,718,419 | 1/1988 | Okada | 128/4 |
| 4,800,870 | 1/1989 | Reid, Jr. . | |
| 4,904,238 | 2/1990 | Williams | 604/264 |
| 4,966,162 | 10/1990 | Wang | 128/750 |
| 4,982,730 | 1/1991 | Lewis, Jr. | 604/22 |
| 4,997,435 | 3/1991 | Demeter | 606/127 |
| 5,037,379 | 8/1991 | Clayman et al. . | |
| 5,084,054 | 1/1992 | Bencini et al. | 606/127 |
| 5,122,147 | 6/1992 | Sewell | 606/113 |
| 5,143,082 | 9/1992 | Kindberg et al. . | |
| 5,147,371 | 9/1992 | Washington et al. . | |
| 5,158,561 | 10/1992 | Rydell et al. . | |
| 5,190,542 | 3/1993 | Nakao et al. | 606/113 |
| 5,195,954 | 3/1993 | Schnepp-Pesch et al. | 606/127 |
| 5,201,740 | 4/1993 | Nakao et al. | 606/113 |
| 5,279,539 | 1/1994 | Bohan et al. | 606/110 |
| 5,312,416 | 5/1994 | Spaeth et al. | 606/110 |
| 5,341,815 | 8/1994 | Cofone et al. | 600/37 |
| 5,354,303 | 10/1994 | Spaeth et al. | 606/113 |
| 5,368,597 | 11/1994 | Pagedas | 606/114 |

OTHER PUBLICATIONS

Abrams, J. S. "A Hard Look at Colonoscopy" The American Journal of Surgery (Jan. 1977) 133:111–115.

Schwesinger, W. H. "Complications in Colonoscopy" Surgery, Gynecology & Obstetrics (Feb. 1979) 148:270–281.

Sugarbaker, P. H. "Colonoscopy in the Management of Diseases of the Colon and Rectum" Surgery, Gynecology & Obstetrics (Sep. 1974) 139:341–349.

Kobayashi, S. "Colonoscopic Polypectomy with Special Reference to Management of Multiple Polyps" (Kitano H. et al.) Gastro. Endosc. (1983) 29, 4:335–6.

ENDOSCOPIC METHOD OF CLEANING AND OPERATING ON A SITE WITHIN A PATIENT

CROSS-REFERENCE TO A RELATED APPLICATION

This application is a continuation-in-part of application Ser. No. 08/333,363 filed Nov. 2, 1994, now pending

BACKGROUND OF THE INVENTION

This invention relates to an endoscopic instrument assembly or device and to an associated endoscopic surgical technique. This invention relates more particularly to an irrigation instrument for use in endoscopic surgery. This invention also relates to an associated endoscopic technique.

In endoscopic diagnostic investigations and surgery, fiber optic instruments are used to visually inspect internal parts of a patient's anatomy through small incisions or natural openings (mouth, anus) in the patient. Frequently, fluids are needed at the distal end of the endoscope to clean a transparent light receiving surface or to clear a site of blood, faeces or other organic debris to facilitate the transmission of optical radiation.

U.S. Pat. No. 5,279,542 discloses an endoscopic instrument comprising an elongate tube provided essentially along its entire length with a channel and further provided within a distal end region with a plurality of longitudinally and circumferentially spaced apertures communicating with the channel. A pressurized source of irrigation fluid is operatively connected to the tube for feeding fluid through the channel and out through the apertures with an essentially uniform radial distribution. The tube is thin enough to fit down the biopsy channel of an endoscope.

Although the instrument of U.S. Pat. No. 5,279,542 works to adequately clean an internal site for purposes of endoscopically investigating that site, the performance of endoscopic surgical operations at the site, for example, the taking of a biopsy or the removal of a polyp, are impeded by the disposition of the endoscopic spraying device in the biopsy channel of the endoscope. This problem is obviated where the endoscope is provided with more than one biopsy channel, either in the insertion tube itself or in a sheath attached to the tube. However, in conventional endoscopes having just one biopsy channel, the endoscopic spraying or cleaning device of U.S. Pat. No. 5,279,542 must be removed and another instrument inserted to take the biopsy or remove the polyp. Frequently, the endoscopic spraying or cleaning device must be reinserted, for purposes of cleaning other sites during the same endoscope examination procedure.

OBJECTS OF THE INVENTION

An object of the present invention is to provide an improved method for providing an irrigating fluid to a distal end of an endoscope or to a surgical site in endoscopic surgery.

Another object of the present invention is to provide an associated instrument or device for use in such a method.

A more particular object of the present invention is to provide such a method which facilitates endoscopic surgery by reducing the time to employ different instruments including an endoscopic irrigation device of the above-described type.

Other objects of the present invention will be apparent from the detailed descriptions and drawings included herein.

SUMMARY OF THE INVENTION

A surgical device comprises, in accordance with the present invention, a primary tubular member having a plurality of lumens and having a diameter sufficiently small so that the tubular member can be inserted through a biopsy channel of an endoscope assembly. A secondary tubular member is slidably inserted in one of the lumens of the primary tubular member. The secondary tubular member has a proximal end provided with a coupling for operatively connecting the secondary tubular member to a source of pressurized liquid. The secondary tubular member has a distal end provided with a multiplicity of apertures spaced from one another both longitudinally and circumferentially along the secondary tubular member so that liquid from the source is ejected from the distal end of the secondary tubular member in a substantially even distribution of jets. An auxiliary endoscopic surgical instrument is slidably disposed in another of the lumens of the primary tubular member for performing a predetermined endoscopic surgical technique.

According to one feature of the present invention, the primary tubular member includes a plurality of cylindrical tubes connected to one another along respective outer surfaces, each of the tubes defining a respective one of the lumens. Alternatively, the primary tubular member includes a single tube defining a longitudinally extending channel, the tube being provided with partition means dividing the channel into the plurality of lumens.

The endoscopic instrument inserted through the other lumen of the primary tubular member may be, for example, an endoscopic graspers, an endoscopic biopsy forceps, an endoscopic cauterization snare, or a laser transmitting optical fiber.

An endoscopic surgical method in accordance with the present invention utilizes an endoscope with an elongate flexible insertion member insertable into a patient, the insertion member having a biopsy channel, and also utilizes (i) a primary tubular member having a plurality of lumens, (ii) a secondary tubular member slidably insertable through one of the lumens and (iii) an auxiliary endoscopic surgical instrument slidably insertable through another of the lumens, the secondary tubular member having a distal end provided with a multiplicity of apertures distributed in a cylindrical locus, i.e., spaced from one another both longitudinally and circumferentially about the distal end of the secondary tubular member. The method includes the steps of (a) inserting the insertion member into a patient, (b) moving the primary tubular member through the biopsy channel so that a distal end of the primary tubular member emerges from the biopsy channel inside the patient, (c) sliding the secondary tubular member in the one of the lumens so that the distal end of the secondary tubular member emerges from the one of the lumens inside the patient, and (d) operatively connecting a proximal end of the secondary tubular member to a source of pressurized liquid. The method further includes the steps of (e) spraying liquid from the source in a substantially uniform cylindrical distribution through the apertures at the distal end of the secondary tubular member, thereby cleaning organic debris from a site inside the patient, (f) ejecting a distal end portion of the endoscopic surgical instrument from the primary tubular member, and (g) using the ejected endoscopic surgical instrument to perform an operation on organic tissues at the site inside the patient upon a cleaning of the site during the step of spraying.

The sliding of the secondary tubular member through the one lumen of the primary tubular member is preferably performed after the distal end of the primary tubular member is moved out of the endoscope biopsy channel. However, in some cases, the distal end of the secondary tubular member may be ejected from the one lumen of the primary tubular member while the distal end of the primary tubular member is still located in the biopsy channel of the endoscope.

The operative connection of the secondary tubular member to the source of pressurized liquid may be implemented, for example, by opening a valve to enable liquid flow from the source and along the secondary tubular member to the apertures. The connection of the secondary tubular member to the source of pressurized liquid may be executed prior to the sliding of the secondary tubular member along the primary tubular member or after the ejection of the distal end of the secondary tubular member from the primary tubular member.

Preferably, the ejecting of the auxiliary endoscopic surgical instrument is effectuated only after the irrigation of the site inside the patient during the spraying step. In many cases, it is only after the cleaning has been accomplished that a strategy can be pursued for treating the site. Upon cleaning the site, it may be clear that a polyp is present which must be removed. In that case, a cauterization snare is inserted through the other lumen of the primary tubular member. The snare is placed about the polyp and electrical current is conducted to the loop and into the organic tissues. Alternatively, the cleaning may reveal an ulcer or other wound which may be treated via a laser mediated cauterization procedure. In that event, a laser transmitting optical fiber is inserted through the primary tubular member and laser radiation is transmitted along the fiber and directed from a distal tip of the fiber to the ulcer or wound.

In another scenario, it is decided that graspers are needed to move or stretch tissues to obtain a better view via the optical components of the endoscope. Using the auxiliary instrument thus includes the step of grasping the organic tissues with the graspers.

Where the auxiliary endoscopic surgical instrument is a biopsy forceps, the forceps are operated to take a biopsy of the organic tissues at the site cleaned by the spray from the irrigation tube, i.e., the secondary tubular member.

Upon the cleaning of the site inside the patient during the spraying irrigation step, a loose piece of organic or inorganic material such as a previously severed polyp may be discovered. In that case, it is useful to insert a Dormia basket through the primary tubular member. The loose material is maneuvered into the basket.

A method in accordance with the present invention facilitates endoscopic investigations and surgical procedures by permitting the irrigation device to remain in place longitudinally traversing the endoscope's insertion member. Thus multiple operations can be performed, for instance, during a removal of the endoscope insertion member from the patient.

DETAILED DESCRIPTION

Figure 1:
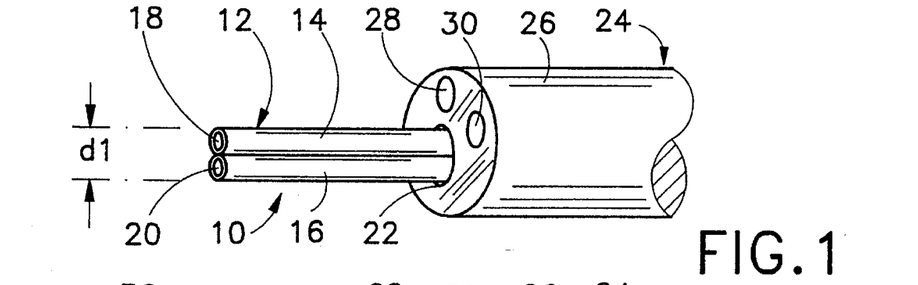
FIG. 1 is a schematic partial perspective view of an endoscope insertion member provided with a tubular instrument guide member in accordance with the present invention.

As illustrated in FIG. 1, an endoscopic surgical device 10 comprises a primary tubular member 12 including a pair of cylindrical tubes 14 and 16 defining respectively lumens 18 and 20. Tubular member 12 has a diameter d1 sufficiently small so that the tubular member can be inserted through a biopsy channel 22 of an endoscope assembly 24. Endoscope assembly 24 includes a flexible insertion member 26 through which a fiber-optic illumination light guide 28 and a fiber-optic image transmission guide 30 extend.

Figure 2:
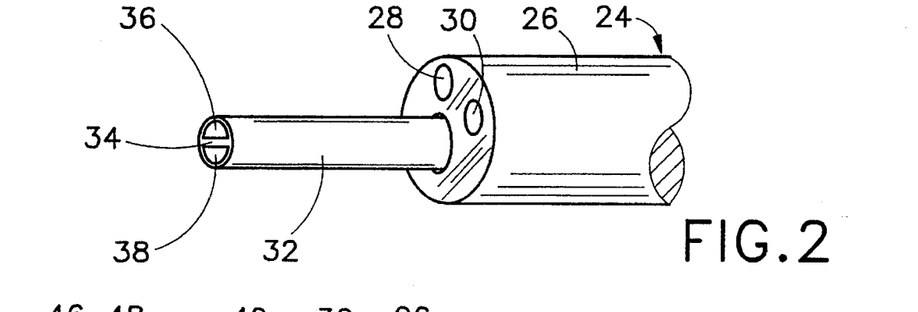
FIG. 2 is a schematic partial perspective view of an endoscope insertion member provided with another tubular instrument guide member in accordance with the present invention.

FIG. 2 illustrates an alternative or equivalent implementation of the assembly shown in FIG. 1. A primary tubular member 32 includes a longitudinally extending partition 34 or series of dividers (not separately illustrated) which compartmentalize a longitudinal channel of tubular member 32 into two lumens 36 and 38.

Figure 3:
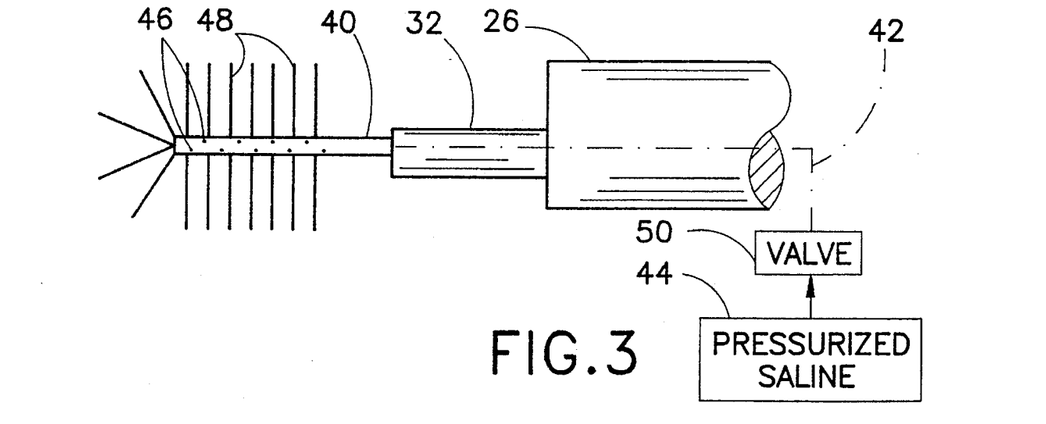
FIG. 3 is a schematic partial side elevational view of the endoscope and instrument guide member of FIG. 1 or FIG. 2, showing an irrigation member inserted through the instrument guide member, in accordance with the present invention.

As depicted in FIG. 3, a secondary tubular member 40 is slidably inserted in one of the lumens 18, 20 or 36, 38 of primary tubular member 12 or 32. For purposes of simplifying the drawing, FIGS. 3–7 carry only the reference designations from FIG. 2. However, it is to be understood that tubular member 12 may be substituted for tubular member 32.

Secondary tubular member 40 has a proximal end provided with a coupling 42 for operatively connecting secondary tubular member 40 to a source 44 of pressurized liquid. Secondary tubular member 40 has a distal end provided with a multiplicity of apertures 46 spaced from one another both longitudinally and circumferentially along member 40 so that liquid from source 44 is ejected from the distal end of secondary tubular member 40 in a substantially even distribution of jets 48 upon an operative connection of tubular member 40 to source 44 via a valve 50.

Figure 4:
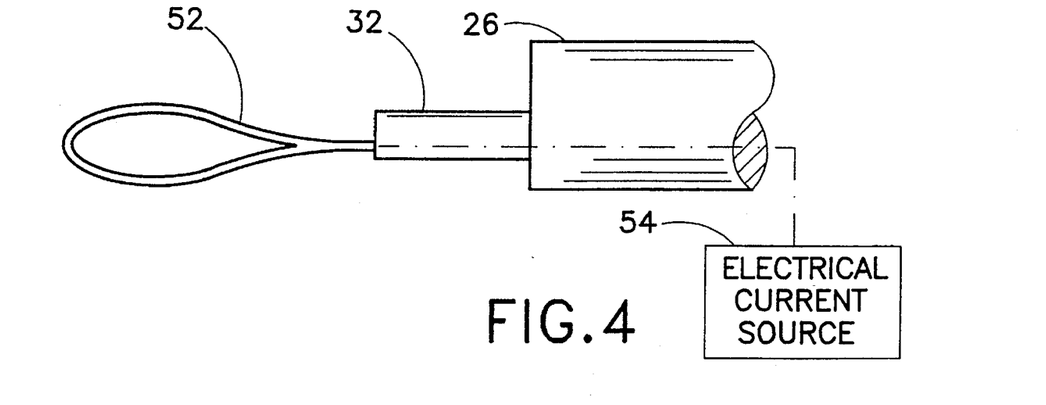
FIG. 4 is a schematic partial side elevational view of the endoscope and instrument guide member of FIG. 1 or FIG. 2, showing an auxiliary endoscopic instrument in the form of a cauterization loop or snare inserted through the instrument guide member, in accordance with the present invention.

As illustrated in FIG. 4, an auxiliary endoscopic surgical instrument exemplarily in the form of a cauterization loop or snare 52 is slidably disposed in another of lumens 38 or 36 of primary tubular member 32 and is operatively connected to a source 54 of electrical current for performing an endoscopic cauterization dissection operation.

Figure 5A:
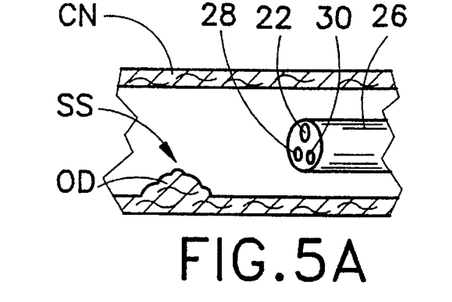
FIGS. 5A–5D are schematic cross-sectional and perspective views, showing use of the instrument assembly of FIGS. 3 and 4 in a procedure in accordance with the present invention.
Figure 5B:
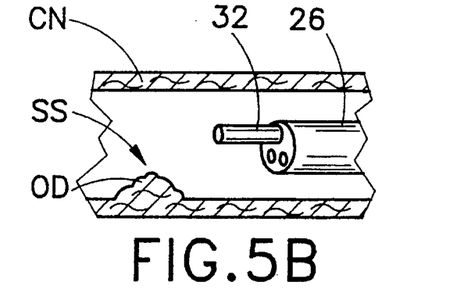
Figure 5C:
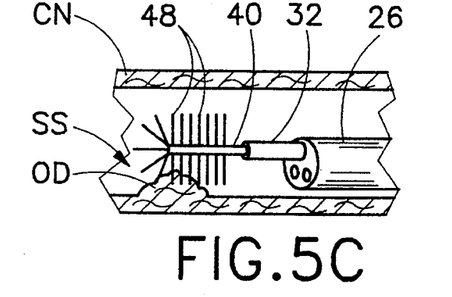
Figure 5D:
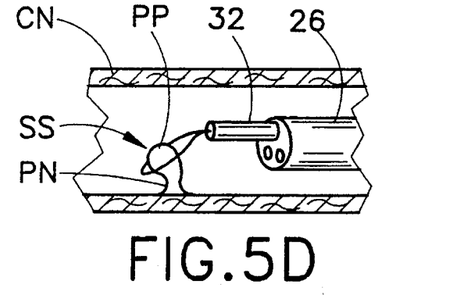

In an endoscopic surgical method utilizing the endoscopic surgical device described hereinabove with reference to FIGS. 1–4, insertion member 26 is introduced into a hollow organ such as a colon CN of a patient, as shown in FIG. 5A. Subsequently, primary tubular member 32 is moved through biopsy channel 22 so that a distal end of the primary tubular member emerges from the biopsy channel inside the patient, as shown in FIG. 5B. Secondary tubular member 40 is then slid through the one lumen 36 or 38 (FIG. 2) so that the distal end of the secondary tubular member emerges from that lumen inside the colon CN of the patient, as depicted in FIG. 5C. Upon the formation of an operatively connection between proximal end 42 of secondary tubular member 40 (FIG. 3) and pressurized liquid source 44, liquid from source 44 is sprayed in a substantially uniform cylindrical distribution through apertures 46 at the distal end of secondary tubular member 40, as shown in FIG. 5C, thereby cleaning organic debris OD from a potential surgical site SS inside colon CN. The clearing of surgical site SS reveals a polyp PP, as shown in FIG. 5D. Upon a decision to remove polyp PP, cauterization snare or loop 52 is ejected from lumen 38 or 36 of primary tubular member 32 (the other lumen 36 or 38 being occupied by secondary tubular member or irrigating instrument 40). The ejected cauterization snare 52 is used to perform a surgical operation removing polyp PP. In accordance with conventional procedures, loop 52 is placed over polyp PP and tightened about a neck PN of that organic structure by shifting primary tubular member 32 in a distal direction relative to snare 52. Upon sufficient closure of snare 52, electrical current is allowed to flow from source 54 through the snare and into the tissues of polyp neck PN. During this procedure, tubular member 32 is shifted further in the distal direction relative to snare 52, to close the loop about polyp neck PN during cauterization thereof.

The sliding of secondary tubular member or irrigating instrument 40 through lumen 36 or 38 of primary tubular member 32 is preferably performed after the distal end of primary tubular member 32 is moved out of endoscope biopsy channel 22. However, in some cases, the distal end of tubular member 40 may be ejected from primary tubular member 32 while the distal end of the primary tubular member is still located in biopsy channel 22 of endoscope insertion member 26.

Figure 6:
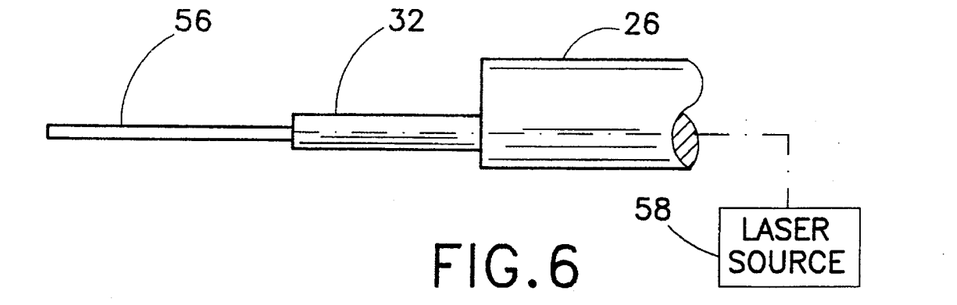
FIG. 6 is a schematic side elevational view of the endoscope and instrument guide member of FIG. 1 or FIG. 2, showing an auxiliary endoscopic instrument in the form of a laser-transmitting optical fiber inserted through the instrument guide member, in accordance with the present invention.

As illustrated in FIG. 6, another auxiliary endoscopic instrument insertable through the other lumen 38, 36 or 20, 18 of primary tubular member 32 or 12 takes the form of a laser-transmitting optical fiber 56 which is operatively connectable to a source 58 of laser radiation. Where the cleaning discussed above with reference to FIG. 5C reveals an ulcer or other wound which may be treated via a laser mediated cauterization procedure or reveals a situation calling for an incision of a particular type, optical fiber 56 is inserted through tubular member 32 in a free channel or lumen thereof. Laser radiation from source 58 is subsequently transmitted along fiber 56 and directed from a distal tip of the fiber to the ulcer or wound (not shown).

Figure 7:
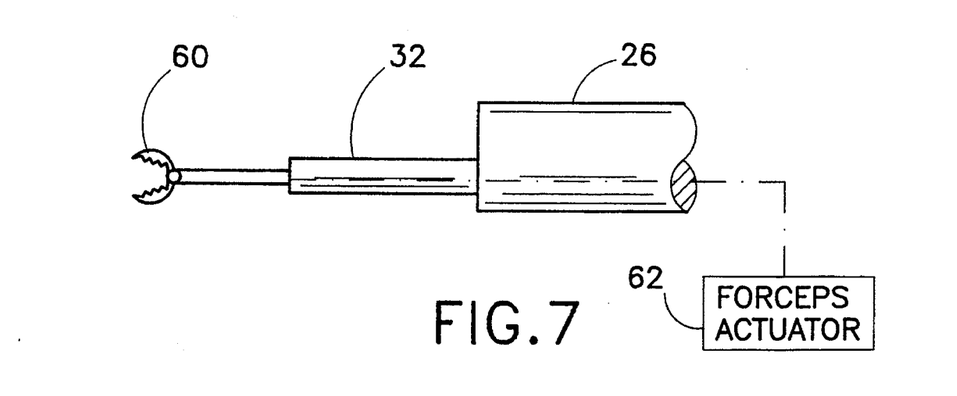
FIG. 7 is a schematic side elevational view of the endoscope and instrument guide member of FIG. 1 or FIG. 2, showing an auxiliary endoscopic instrument in the form of a forceps inserted through the instrument guide member, in accordance with the present invention.

As depicted in FIG. 7, a further auxiliary endoscopic surgical type instrument insertable through the free or ancillary lumen 38, 36 or 20, 18 of primary tubular member 32 or 12 is a forceps 60, e.g., a grasping forceps or a biopsy forceps. Where the auxiliary endoscopic surgical instrument is a biopsy forceps, the forceps are operated via an actuator 62 to take a biopsy of the organic tissues at the site SS. Grasping forceps are used to move or stretch tissues, for example, to obtain a better view via the optical components 28 and 30 of endoscope assembly 24 (FIGS. 1 and 2).

Preferably, the ejecting of the auxiliary endoscopic surgical instrument 52, 56, or 60 is effectuated only after the irrigation of the potential surgical site SS during the spraying or irrigating procedure (FIG. 5C). In many cases, it is only after the cleaning has been accomplished that a decision can be made as to which auxiliary endoscopic surgical instrument 52, 56, 60 is appropriate for treating the organic material at site SS.

Figure 8:
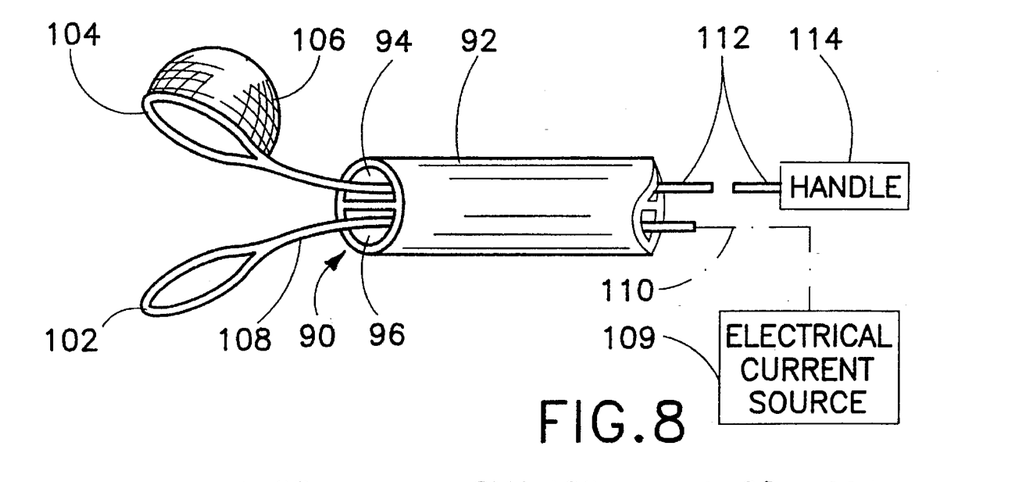
FIG. 8 is a schematic side perspective view, on an enlarged scale, of an endoscopic surgical instrument assembly incorporating a dual lumen tubular member for insertion through an endoscope biopsy channel.

As illustrated in FIG. 8, a related surgical instrument assembly 90 for use in snare cauterization operations comprises a tubular instrument guide member 92 defining a plurality of separate longitudinally extending lumens 94 and 96. Lumens 94 and 96 have semi-circular cross-sections. Tubular member 92 has a diameter sufficiently small so that the tubular member can be inserted through a biopsy channel 98 of a flexible endoscope insertion member 100 (FIGS. 9A–9E). Instrument assembly 90 further comprises a cauterization loop 102 and an auxiliary loop 104 which is provided with a flexible web member 106 defining an alternately expandable and contractible capture pocket. Auxiliary loop 104 defines a mouth opening of the pocket.

Figure 9A:
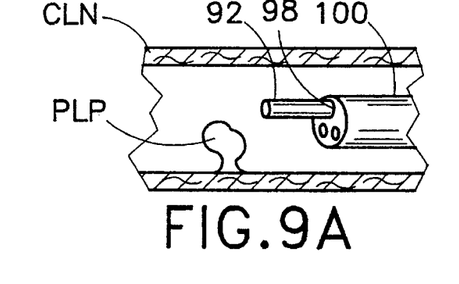
FIGS. 9A–9E are partially schematic cross-sectional views of a colon and partially schematic side perspective views of an endoscope incorporating the instrument assembly of FIG. 8, showing successive steps in the performance of an endoscopic operation.

An electrically conductive wire 108 is connected to cauterization loop 102, cauterization loop 102 and wire 108 being disposed at least partially in lumen 96 of tubular member 92. An electrical supply 109 is operatively connected to wire 108 via a coupling 110 for feeding an electrical current to cauterization loop 102 via wire 108. An elongate flexible shifting member 112 (e.g., a wire) is connected at one end to auxiliary loop 104. Auxiliary loop 104 and wire 112 are at least partially disposed in lumen 94 of tubular member 92. A handle assembly 114 is provided at the proximal end of wire 112 for facilitating the maneuvering of auxiliary loop 104 from outside the patient. Handle assembly 114 may also be connected to cauterization loop 102 to facilitate the manipulation of the loop to eject the loop from lumen 96 and to place the loop about a polyp PLP (FIG. 9A). Handle assembly 114 is operatively connected to cauterization loop 102 and auxiliary loop 104 so as to allow those two elements to be ejected independently from tubular member or catheter 92.

Web member 106, whether a net or a continuous film of polymeric material, may be connected to auxiliary loop 104 at a plurality of spaced locations, e.g., via ringlets (not shown). Tubular member 92 is preferably flexible so that it may pass along bends in endoscope insertion member 100 upon a deployment thereof during an endoscopic investigation.

As depicted in FIG. 9A, upon introduction of endoscope insertion member 100 into a patient's colon CLN and use of the endoscope assembly to visually monitor internal body tissues of the patient to locate polyp PLP, tubular member 92 is moved in a distal direction through biopsy channel 98 of endoscope insertion member 100 to eject a distal end portion of the tubular member from the biopsy channel.

Figure 9B:
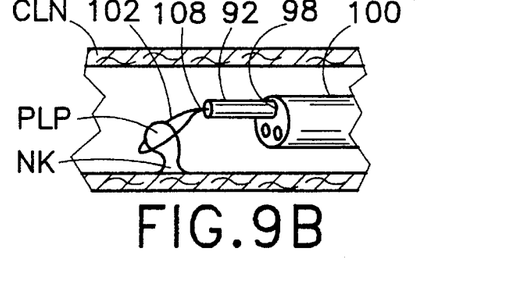

Subsequent steps of an endoscopic surgical procedure are depicted in FIG. 9B. Cauterization snare 102 is shifted in a distal direction relative to ejected tubular member 92 to eject the cauterization loop from the tubular member. Upon ejection, ejected cauterization loop 102 is expanded from a collapsed configuration inside tubular member 92 to an opened configuration. Cauterization loop 102 is then manipulated from outside of the patient to pass the expanded cauterization loop over polyp PLP which is to be removed from the patient.

Figure 9C:
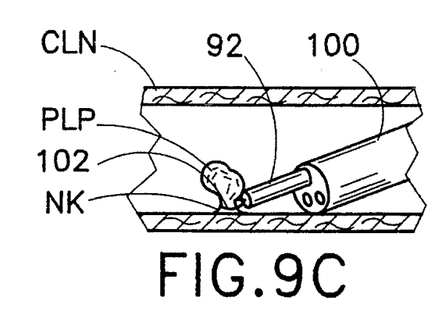

As illustrated in FIG. 9C, cauterization loop 102 is at least partially closed to engage polyp PLP around a base region or neck NK thereof. This closure is effectuated by shifting tubular member 92 and cauterization snare relatively towards one another to thereby at least partially withdraw or retract cauterization loop 102 into tubular member 92. Upon closure of cauterization loop 102 about polyp neck NK, an electrical current is conducted through wire 108 and cauterization loop 102 to burn through polyp PLP at base region or neck NK thereof, thereby severing the polyp at the neck.

Figure 9D:
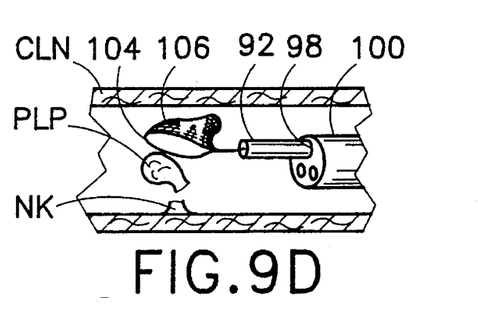
Figure 9E:
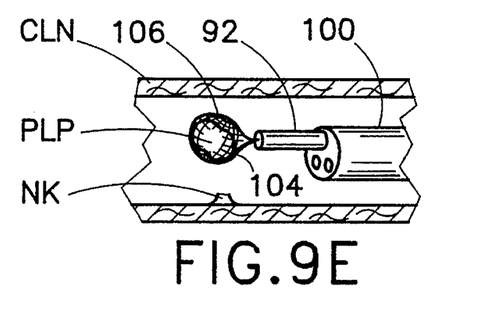

Upon a severing of the polyp PLP at the neck NK, cauterization loop 102 is retracted into tubular member 92. Then, auxiliary loop 104 is ejected from tubular member 92, the auxiliary loop and web member or capture pocket 106 being opened from a folded configuration inside lumen 94 of tubular member 92 to an at least partially expanded or opened configuration, as illustrated in FIG. 9D. Subsequently, auxiliary loop 104 is maneuvered from outside the patient to pass the opened auxiliary loop 104 over the severed polyp PLP so that web member or pocket 106 substantially surrounds the polyp. At that juncture, auxiliary loop 104 is at least partially closed to capture the severed polyp PLP in web member or pocket 106, as shown in FIG. 9E. As further indicated in FIG. 9E, the closing of auxiliary loop 104 includes shifting tubular member 92 and the auxiliary loop relatively towards one another to thereby at least partially withdraw auxiliary loop 104 into tubular member 92. After capture has been effectuated, polyp PLP is removed from the patient together with auxiliary loop 104 and the capture pocket 106.

Biopsy channel 98 of endoscope member 100 may be located in a sheath disposed on the endoscope, as described in U.S. Pat. No. 5,217,001, the disclosure of which is hereby incorporated by reference.

Figure 10A:
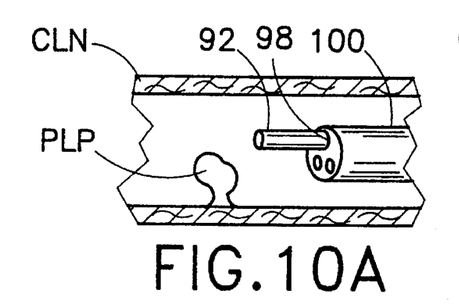
FIGS. 10A–10F are partially schematic cross-sectional views similar generally to FIGS. 9A–9E, showing an alternative series of successive steps in an endoscopic operation.

FIGS. 10A–10E depict a sequence of steps in another endoscopic polyp removal procedure. FIG. 10A is identical to FIG. 9A and shows endoscope insertion member 100 inserted into colon CLN. Insertion member 100 is used to visually monitor internal body tissues of the patient to locate polyp PLP. Upon locating polyp PLP, the endoscopist moves tubular member 92 in a distal direction through biopsy channel 98 of endoscope insertion member 100 to eject the distal end portion of the tubular member from the biopsy channel.

Figure 10B:
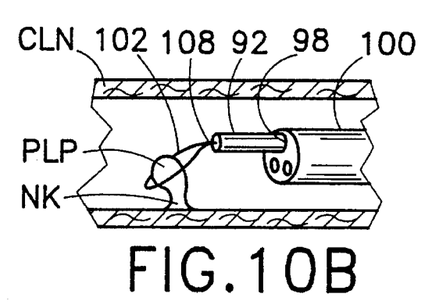

FIG. 10B is identical to FIG. 9B and illustrates subsequent steps of the endoscopic polyp removal procedure. Cauterization loop 102 is shifted in a distal direction relative to ejected tubular member 92 to eject the cauterization loop from the tubular member. Upon ejection, ejected cauterization loop 102 is expanded from a collapsed configuration inside tubular member 92 to an opened configuration. Cauterization loop 102 is then manipulated from outside of the patient to pass the expanded cauterization loop over polyp PLP which is to be removed from the patient.

Figure 10C:
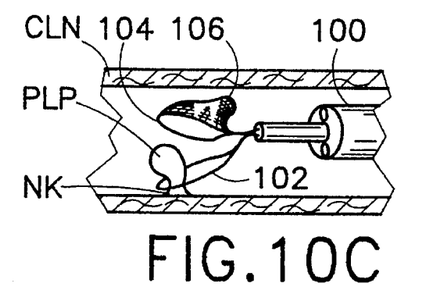
Figure 10D:
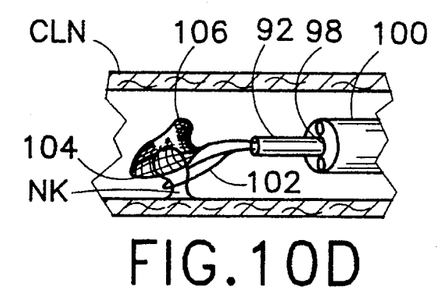
Figure 10E:
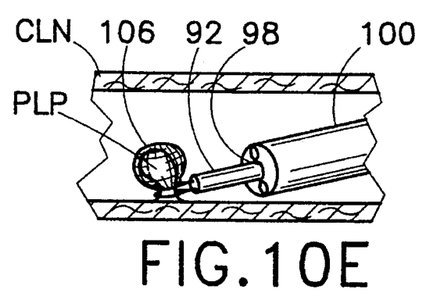

As illustrated in FIG. 10C, cauterization loop 102 is maneuvered to encircle polyp PLP around base region or neck NK thereof. Prior to completing a closure of cauterization loop 102 about polyp PLP, auxiliary loop 104 and capture pocket 106 are ejected from tubular member 92 and are opened from a folded configuration inside lumen 94 of tubular member 92 to an at least partially expanded or opened configuration. As illustrated in FIG. 10D, auxiliary loop 104 is then maneuvered from outside the patient to pass the opened auxiliary loop 104 and capture pocket 106 over the polyp PLP so that web member or pocket 106 substantially surrounds the polyp. At that juncture, tubular member 92 on the one hand and cauterization loop 102 and auxiliary loop 104 on the other hand are shifted relatively towards one another to thereby effectuate a partial closure of the loops about polyp PLP, particularly about neck region NK thereof, as shown in FIG. 10E.

Figure 10F:
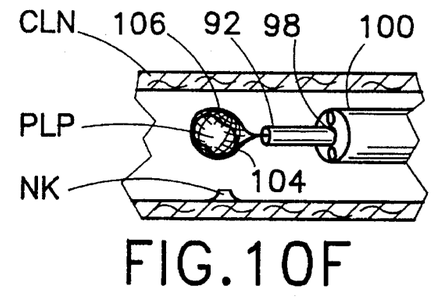

Upon closure of cauterization loop 102 about polyp neck NK, an electrical current is conducted through wire 108 and cauterization loop 102 to burn through polyp PLP at base region or neck NK thereof, thereby severing the polyp at the neck. Simultaneously with the current flow, cauterization loop 102 is drawn into tubular member 92. The severed polyp is automatically or naturally captured within pocket 106, as illustrated in FIG. 10F. After capture has been effectuated, polyp PLP is removed from the patient together with auxiliary loop 104 and the capture pocket 106.

Although the invention has been described in terms of particular embodiments and applications, one of ordinary skill in the art, in light of this teaching, can generate additional embodiments and modifications without departing from the spirit of or exceeding the scope of the claimed invention. Accordingly, it is to be understood that the drawings and descriptions herein are proffered by way of example to facilitate comprehension of the invention and should not be construed to limit the scope thereof.

What is claimed is:

1. An endoscopic surgical method comprising the steps of:

providing an endoscope with an elongate flexible insertion member insertable into a patient, said insertion member having a biopsy channel;

also providing (i) a primary tubular member having a plurality of lumens, (ii) a secondary tubular member slidably insertable through one of said lumens and (iii) an auxiliary endoscopic surgical instrument slidably insertable through another of said lumens, said secondary tubular member having a distal end provided with a multiplicity of apertures distributed in a cylindrical locus;

inserting said insertion member into a patient;

moving said primary tubular member through said biopsy channel so that a distal end of said primary tubular member emerges from said biopsy channel inside the patient;

sliding said secondary tubular member in said one of said lumens so that the distal end of said secondary tubular member emerges from said one of said lumens inside the patient;

operatively connecting a proximal end of said secondary tubular member to a source of pressurized liquid;

upon completion of said steps of inserting, moving sliding and connecting, spraying liquid from said source in a substantially uniform cylindrical distribution through said apertures at the distal end of said secondary tubular member, thereby cleaning organic debris from a site inside the patient;

ejecting a distal end portion of said instrument from said another of said lumens inside the patient; and upon ejection of the distal end portion of said instrument and upon a cleaning of said site during said step of spraying, using said instrument to perform an endoscopic surgical operation on organic tissues at said site.

2. The method defined in claim 1 wherein said step of sliding is performed after said step of moving.

3. The method defined in claim 1 wherein said step of operatively connecting includes the step of opening a valve to enable liquid flow from said source and along said secondary tubular member to said apertures.

4. The method defined in claim 1 wherein said step of ejecting is performed after said step of spraying.

5. The method defined in claim 1 wherein said instrument is an endoscopic graspers, said step of using said instrument including the step of grasping said organic tissues with said graspers.

6. The method defined in claim 1 wherein said instrument is an endoscopic biopsy forceps, said step of using said instrument including the step of taking a biopsy of said organic tissues.

7. The method defined in claim 1 wherein said instrument is an endoscopic cauterization snare, said step of using said instrument including the steps of placing said snare about said organic tissues and conducting electrical current to said loop and into said organic tissues.

8. The method defined in claim 1 wherein said instrument is a laser transmitting optical fiber, said step of using said instrument including the steps of transmitting laser radiation along said fiber and directing said laser radiation from a distal tip of said fiber to said organic tissues.

* * * * *